United States Patent [19]

Cottman

[11] 4,311,637
[45] Jan. 19, 1982

[54] POLYPHENOLIC ESTERS OF MERCAPTOPHENOLS AS ANTIOXIDANTS

[75] Inventor: Kirkwood S. Cottman, Akron, Ohio

[73] Assignee: The Goodyear Tire & Rubber Company, Akron, Ohio

[21] Appl. No.: 119,692

[22] Filed: Feb. 8, 1980

[51] Int. Cl.$^3$ .................. C08K 5/36; C07C 149/40
[52] U.S. Cl. ...................... 260/45.85 B; 560/17
[58] Field of Search .................. 260/45.85 B; 560/17

[56] References Cited

U.S. PATENT DOCUMENTS

| | | | |
|---|---|---|---|
| 3,536,661 | 10/1970 | Hagemeyer et al. | 560/17 |
| 3,637,809 | 1/1972 | Kleiner | 560/17 |
| 3,649,667 | 3/1972 | Song et al. | 260/45.85 B |
| 3,751,483 | 8/1973 | Cisney | 560/17 |
| 3,989,741 | 11/1976 | Parker | 260/45.85 R |
| 4,168,387 | 9/1979 | Cottman | 260/45.85 E |

*Primary Examiner*—V. P. Hoke
*Attorney, Agent, or Firm*—D. O. Nickey

[57] ABSTRACT

There is disclosed polyphenolic mercaptophenol type antioxidants, a method of preparing the antioxidants and to polymer compositions containing such polyphenolic mercaptophenol type antioxidants. In particular, polyphenolic antioxidants such as 2-(2-hydroxy-3-tertiary-butyl-5-methylbenzyl)-4-methyl-6-tertiary butyl phenyl 3-(4-hydroxyphenylthio)propionate.

20 Claims, No Drawings

POLYPHENOLIC ESTERS OF MERCAPTOPHENOLS AS ANTIOXIDANTS

TECHNICAL FIELD

This invention relates to new polyphenolic mercaptophenol type antioxidants, to a method of preparing the antioxidants and to polymer compositions containing such polyphenolic mercaptophenol type antioxidants. In particular, polyphenolic antioxidants such as 2-(2-hydroxy-3-tertiary-butyl-5-methylbenzyl)-4-methyl-6-tertiary butyl phenyl 3-(4-hydroxyphenylthio) propionate and 2-(3,5-ditertiarybutyl-4-hydroxybenzyl)-4-methylphenyl 3-(4-hydroxyphenylthio)propionate, and a process for synthesizing said polyphenolic antioxidants involving the reaction between a phenolic compound with ester forming compounds to form an "intermediate ester" and a subsequent reaction of the "intermediate ester" with a mercaptophenol to provide the compounds of this invention.

BACKGROUND ART

The prior art teaches that antioxidant activity in phenolic compounds occurs because of hydrogen extraction from the hydroxyl groups, see Scott, *Atmospheric Oxidation of Antioxidants*, Chapter IV (1965). It has been found according to the present invention that esterification of phenolic compounds and a subsequent reaction with a mercaptophenol produces an antioxidant with significantly enhanced antioxidant activity.

It is known that essentially all types of organic polymers, both natural and synthetic, and particularly rubbers from dienes are susceptible to deterioration resulting from prolonged exposure to oxidative aging. Unfortunately many of the commercially used stabilizers are often volatilized when the polymeric products are exposed to elevated temperature and/or high vacuum over a prolonged period of time. Furthermore, these known antioxidants are rather quickly extracted from polymeric compositions by repeated washing with aqueous detergent solutions or organic solvents. These severe conditions are routinely encountered by rubberized garments or garments containing rubber when they are subjected to frequent laundering or dry cleaning.

Attempts to remedy these problems are disclosed in references such as U.S. Pat. Nos. 3,714,122; 3,952,402; 3,962,187; 3,645,970; 3,305,552; 3,699,172; 3,728,399; 3,984,372; German Pat. No. 1,931,452, Canadian Pat. No. 955,349 and Canadian Pat. No. 979,594. U.S. Pat. No. 3,553,163 took a prior art compound 4-methylthiol phenol and discovered that by placing a substituent on a ring he could improve the antioxidative activity of the compounds. None of these references, however, discloses or suggests the use of polyphenolic esters of mercaptophenols as antioxidants for organic compositions which tend to deteriorate by absorption of oxygen. Thus, it is evident that polyphenolic antioxidants which provide solutions to the problems of antioxidant extraction and low antioxidative activity would be an advancement over presently known antioxidants.

DISCLOSURE OF INVENTION

The present invention relates to a process for the production of a polyphenolic mercaptophenol antioxidant and its use in oxidizable polymers and organic materials. The invention pertains to an antioxidant having one of the following formulas:

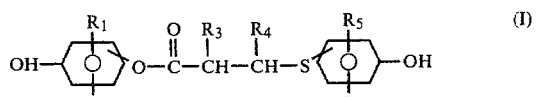

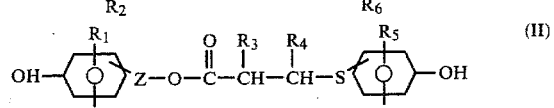

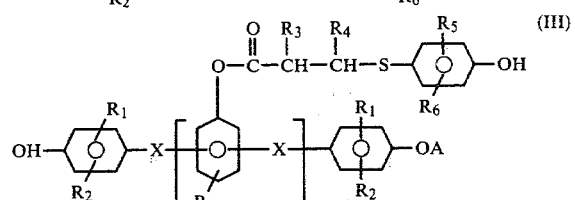

wherein A is a hydrogen radical or a radical of the structural formula:

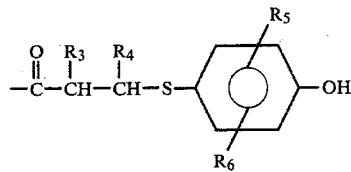

and wherein $R_1$ and $R_2$ are the same or different radicals selected from the group consisting of hydrogen, alkyl radicals containing 1 to 9 carbon atoms, aralkyl radicals containing 7 to 9 carbon atoms, and aryl radicals and alkylaryl radicals having from 7 to 9 carbon atoms; $R_3$ and $R_4$ are hydrogen or methyl radicals; and $R_5$ and $R_6$ are the same or different radicals selected from the group consisting of alkyl radicals containing from 1 to 9 carbon atoms, aryl radicals and aralkyl radicals having from 7 to 9 carbon atoms; and wherein Z is an alkylene radical having from 1 to 9 carbon atoms, and wherein X is the same or different radical selected from the group consisting of:

1. cyclic dienes with nonadjacent carbon to carbon double bonds within the ring structure containing from 5 to 20 carbon atoms from which the bivalent radicals are prepared, and 2. a bivalent radical selected from the group consisting of

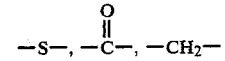

and wherein n is selected from the group consisting of 0 and real numbers 1 to 5 with the provision that when n equals 0, A is not a hydrogen radical.

The antioxidants of this invention are "partial esters" of polyphenolic mercaptophenols. The term "partial esters" is used to mean an esterified polyphenol in which less than all of the phenolic hydroxyl groups of the phenol are esterified.

The compounds of this invention are prepared by reacting a phenolic compound selected from the group comprised of the following structural formulae:

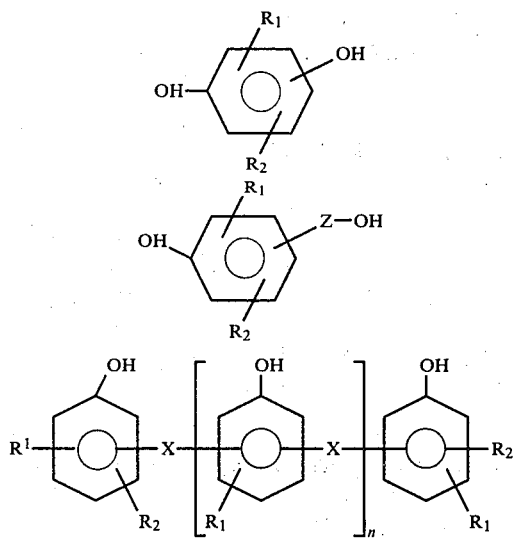

wherein $R_1$, $R_2$, $R_3$, $R_4$, X, Z and n are as above.

The selected phenolic compound is reacted with a compound of the structure:

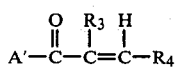
(VII)

wherein $R_3$ and $R_4$ are as described above and A' is selected from the group comprised of chlorine, bromine, iodine; in the presence of a well-known acid acceptor. It is desirable to use suitable acid acceptors such as triethylamine, pyridine, sodium carbonate or sodium bicarbonate to yield the intermediate esters with a formula selected from:

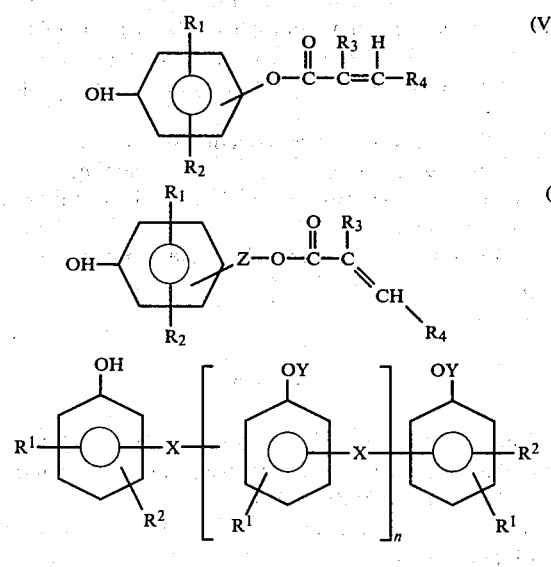

wherein Y is hydrogen or

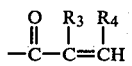

and $R_1$, $R_2$, $R_3$, $R_4$, X, Z and n are as above.

The ester intermediate with structural formulas VIII, IX and X are reacted with a mercaptophenol of the structural formula:

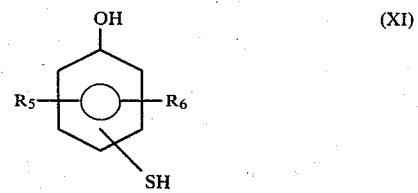
(XI)

wherein $R_5$ and $R_6$ are the same or different radicals selected from the group consisting of hydrogen, alkyl radicals containing from 1 to 9 carbon atoms, aralkyl radicals containing from 7 to 9 carbon atoms and aryl radicals.

The ester intermediate is reacted with the mercaptophenol in the presence of a catalyst commonly known to the art, such as an alkali metal hydroxide, to yield the products of this invention with one of the above structural formulas I, II or III.

The compound prepared in Example 6 was prepared from a commercially available antioxidant known as 2,2'-methylene bis(4-methyl-6-tertiary butyl phenol). However, any other conventionally known phenolic antioxidant is a suitable starting material. Thus, this invention can encompass nearly all phenolic antioxidants. By the reaction of this invention higher molecular weight less volatile and more persistent antioxidants are prepared with usually 2 to 4 times the antioxidative activity of the starting phenolic material.

While the preparation of known antioxidants is well-known it must be realized that the present invention through the esterification and subsequent reaction with a mercaptophenol yields an antioxidant that is far superior to the starting material.

The polymers that may be conveniently protected by the compounds described herein are oxidizable vulcanized and unvulcanized polymers susceptible to oxygen degradation, such as natural rubber, balata, gutta percha and oxidizable synthetic polymers including those containing carbon to carbon double bonds, such as rubbery diene polymers, both conjugated and nonconjugated. Representative examples of the synthetic polymers used in the practice of this invention are polychloroprene, homopolymers of a conjugated 1,3-diene such as isoprene and butadiene, and in particular, polyisoprenes and polybutadienes having essentially all of their repeat units combined in a cis-1,4 structure; copolymers of a conjugated 1,3-diene such as isoprene and butadiene with up to 50 percent by weight of at least one copolymerizable monomer including ethylenically unsaturated monomers such as styrene and acrylonitrile butyl rubber, which is a polymerizable product of a major proportion of a monoolefin and a minor proportion of a multiolefin such as butadiene or isoprene; polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene such as dicyclopentadiene, 1,4-hexadiene, ethylidene norbornene and methylene norbornene. Lubricating oils and polyesters may also be protected.

Polyphenolic antioxidants of this invention may be used with or without other stabilizers, vulcanizing agents, accelerators or other compounding ingredients. In order to effectively stabilize polymers, small proportions of one or more of the phenolic antioxidants in accordance with this invention are added to the polymer in a customary antioxidant amount which may vary somewhat depending upon the type and requirements of the polymers to be produced. The compounds of this invention are useful in protecting polymer in any form, for example, polymers in latex form, unvulcanized polymer and vulcanized polymer.

The method of addition of the antioxidant to the polymer is not critical. It may be added by any of the conventional means such as by adding to a polymer latex, milling on an open mill or by internal mixing.

Normally from about 0.001 part to about 10.0 parts of the antioxidant by weight based on the weight of the polymers can be used, although the precise amount of these effective stabilizers which is to be employed will depend somewhat on the nature of the polymer and the severity of the deteriorating conditions to which the polymer is to be exposed. In unsaturated polymers such as those made from conjugated dienes, e.g. rubbery butadiene/styrene polymers, the amount of antioxidant necessary is greater than that required by saturated polymers such as polyethylene.

The following examples illustrate and are not intended to limit the practice of the present invention.

EXAMPLE 1

In a one liter flask equipped with a stirring rod, thermometer, and water condenser 324 grams of para cresol and 5½ grams of $BF_3$ etherate were heated to 90° C. To the mixture was added dropwise 132 grams of dicyclopentadiene. The product was distilled to a pot temperature of 195° C. at 24 mm Hg. The residue of 300 grams was dissolved in 300 ml of toluene. After adding 24 grams of toluene sulfonic acid, isobutylene was added at 60° to 75° C. until no more would react. The butylated product was neutralized with 24 grams of $Na_2CO_3$ in aqueous solution and decanted. The solvent was distilled from the product to a pot temperature of 175° C. at 25 mm Hg. Weight of product 353 grams.

EXAMPLE 2

Two hundred grams of a product prepared as described in Example 1 was dissolved in 150 ml. tetrahydrofuran and 70 grams of triethylamine. Dropwise 52 grams of acryloyl chloride was added at 35° to 40° C. The flask contents were reacted two hours longer and then diluted with 150 ml. of toluene. The reaction product was washed with water and decanted. It was distilled in the presence of one gram $Na_2CO_3$ to a pot temperature of 173° C. at 31 mm Hg. Hydroxyl number is 99.

EXAMPLE 3

One hundred grams of the product prepared in Example 2 was dissolved in 150 ml. of toluene. Then 8.4 grams of 4-mercaptophenol and 2 pellets KOH (dissolved in a little ethanol) was added. The flask contents were reacted at 55° C. for 5 hours at which time gas chromatography indicated that all the 4-mercaptophenol had reacted. The volatiles were distilled off to a pot temperature of 184° C. at 35 mm Hg. Weight residue 110 grams. % Sulfur 2.14. Hydroxyl number is 128.

EXAMPLE 4

Same as Example 3 except 40 grams of the product prepared in Example 2, 100 ml. of toluene, 6.7 grams of 4-mercaptophenol and one pellet KOH were used. Weight residue 46 grams, % Sulfur 3.35, Hydroxyl number 143.

EXAMPLE 5

Same as Example 3 except 40 grams of the product prepared in Example 2, 100 ml. of toluene, one pellet KOH and 13.7 grams of 4-mercaptophenol were used. Weight residue 53 grams, % Sulfur 5.80, Hydroxyl number 177.

EXAMPLE 6

Fifty grams of 2-(2-hydroxy-3-tertiary butyl-5-methylbenzyl)-4-methyl-6-tertiary butylphenylacrylate, 20.2 grams of 4-mercaptophenol, one pellet KOH (dissolved in ethanol) were dissolved in 100 ml. of benzene. When the reaction was finished as evidenced by thin layer chromatography the product was distilled to a pot temperature of 180° C. at 1.0 mm. Hg. The product was 2-(2-hydroxy-3-tertiary butyl-5-methylbenzyl)-4-methyl-6-tertiary butyl phenyl 3-(4-hydroxyphenylthio) propionate.

EXAMPLE 7

To a flask is added 27 grams of 3,5-ditertiarybutyl-4-hydroxyphenylacrylate, 13 grams of 4-mercaptophenol, 1.0 grams of trimethylbenzylammonium hydroxide (40% in methanol), 5 ml. ethanol and 100 ml. of toluene. The flask contents are reacted at 50° C. for 6 hours. The solvents are removed by mild distillation. The product was characterized as 3,5-ditertiary-4-hydroxyphenyl 3-(4-hydroxyphenylthio)propionate.

EXAMPLE 8

To a flask is added 32 grams of 3-(3,5-ditertiary butyl-4-hydroxyphenyl)propylacrylate, 12 grams of 4-mercaptophenol, 2 pellets KOH (dissolved in 5 ml. of denatured ethanol) and 100 ml. of toluene. The reaction is followed by thin layer chromatography until complete. The product is [3-(3,5-ditertiarybutyl-4-hydroxyphenyl)propyl]3-(4-hydroxyphenylthio) propionate.

The precise amount of antioxidant depends upon the particular polymer and conditions to which it will be exposed. Generally, the amount employed for antioxidative purposes varies between 0.001 and 10 parts per hundred parts of polymer. The preferred range of use is from 0.5 to 2.5 parts per hundred of rubber.

In order to evaluate the effectiveness of the compounds of this invention as a stabilizer for polymers, the compounds were incorporated into an oxidizable polymer. The following example is presented to illustrate and not to limit the use of the compounds of the present invention.

The compounds of this invention have been evaluated by the oxygen absorption test. The oxygen absorption tests were conducted by dissolving in toluene portions of an unstabilized SBR 1006 polymer. The toluene contained the antioxidant to be tested at a level of 1.00 part of antioxidant per 100 parts of SBR 1006 polymer. The cements so formed were poured onto aluminum foil so as to form a thin film. After drying, the weight of rubber was obtained in connection with each sample. Thereafter, the foil with the adhering rubber strip was placed in the oxygen absorption apparatus. The time required for each sample to absorb 1.0 percent oxygen was determined and recorded in the following Table I. This testing procedure is described in further detail in *Industrial and Engineering Chemistry*, 43, p. 456 (1951) and *Industrial and Engineering Chemistry*, 45, p. 392 (1953).

The following are results obtained in SBR 1006 at the 1.0 part level at 100° C.

| Antioxidant | Hours to Absorb 1.0% Oxygen |
|---|---|
| Example I (Control) | 363 |
| Example II (Control) | 412 |
| Example III | 1071 |
| Example IV | 1161 |
| Example V | 1273 |
| Example VI | 991 |
| Example I (Control) | 358 |
| None | <20 |

INDUSTRIAL APPLICABILITY

It is evident from the invention disclosed herein that the esterification and subsequent reaction with a mercaptophenol of a phenolic compound such as 2,2'-methylene bis(4-methyl-6-tertiarybutyl phenol) will produce compounds of enhanced antioxidative ability. The industrial applications are readily apparent in light of the enhanced antioxidative ability of from 2 to 4 times more than the starting material. Use of such high molecular weight nonvolatile antioxidants will greatly lessen the removal of antioxidants from rubber polymers so as to overcome the problem of antioxidant extraction. For example, the use of polymers in automotive applications as gaskets, subjects polymers to high temperatures for great periods of time thereby requiring long lasting and persistent protection.

While certain representative embodiments and details have been shown for the purpose of illustrating the invention it will be apparent to those skilled in this art that various changes and modifications may be made therein without departing from the spirit or scope of this invention.

I claim:

1. A polymer subject to oxidation having incorporated therein an antioxidant amount of a composition of matter conforming to the following structural formula:

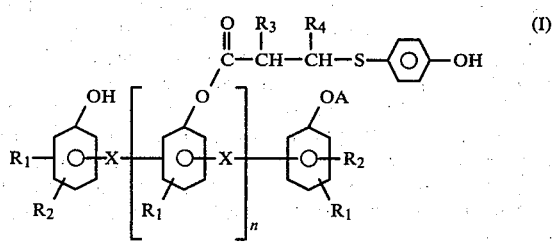

wherein A is hydrogen or a radical of the structural formula:

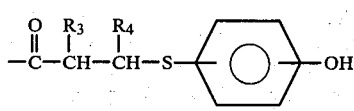

and R₁ and R₂ are the same or different radicals selected from the group consisting of hydrogen radicals, alkyl radicals containing from 1 to 9 carbon atoms, aralkyl radicals containing from 7 to 9 carbon atoms, aryl radicals and alkylaryl radicals having from 7 to 9 carbon atoms; and wherein $R_3$ and $R_4$ are hydrogen or methyl radicals; and wherein X is the same or different radicals selected from the group consisting of cyclic dienes with nonadjacent carbon to carbon double bonds within the ring structure containing 5 to 20 carbon atoms from which the divalent radicals are prepared and a methylene radical of the formula —$CH_2$—, and wherein n is selected from the group consisting of 0 and real numbers 1 to 5 with the provision that when n equals 0, A is never hydrogen.

2. A polymer according to claim 1 wherein $R_1$ and $R_2$ are ortho with respect to the phenolic hydroxyl group.

3. A polymer according to claim 1 wherein $R_1$ and $R_2$ are hydrogen and the phenolic hydroxyl group is para to the radical X.

4. A polymer according to claim 1 wherein $R_1$ and $R_2$ are tertiary-butyl radicals and ortho to the phenolic hydroxyl group.

5. A polymer according to claim 1 wherein X is a divalent dicyclopentadiene radical.

6. A polymer according to claim 1 wherein X is a divalent 2,5-norbornadiene radical.

7. A polymer according to claim 1 wherein X is a divalent methylene radical.

8. A polymer according to claim 1 that has incorporated therein 2-(2-hydroxy-3-tertiary-butyl-5-methylbenzyl)-4-methyl-6-tertiary-butyl phenyl-3-(4-hydroxy phenylthio) propionate.

9. A polymer according to claim 1 that has incorporated therein 3,5-ditertiary butyl-4-hydroxyphenyl-3-(4-hydroxyphenylthio)propionate.

10. A polymer according to claim 1 that has incorporated therein [3-(3,5-ditertiary butyl-4-hydroxyphenyl)-propyl]-3-(4-hydroxyphenylthio) propionate.

11. A composition of matter conforming to the following structural formula:

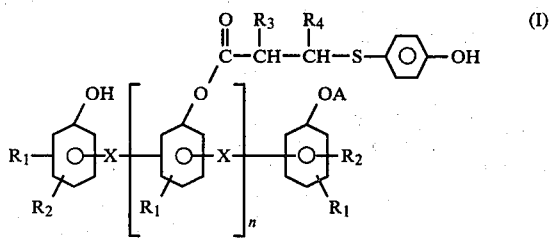

wherein A is a hydrogen radical or radical of the structural formula:

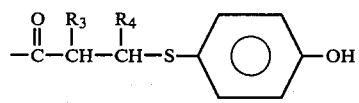

and $R_1$ and $R_2$ are the same or different radicals selected from the group consisting of hydrogen radicals, alkyl radicals containing from 1 to 9 carbon atoms, aralkyl radicals containing from 7 to 9 carbon atoms, aryl radicals and alkylaryl radicals having from 7 to 9 carbon atoms; and wherein $R_3$ and $R_4$ are hydrogen or methyl radicals; and wherein X is the same or different radical selected from the group consisting of cyclic dienes with nonadjacent carbon to carbon double bonds within the ring structure containing 5 to 20 carbon atoms from which the divalent radicals are prepared and a methylene radical of the formula —$CH_2$—, and wherein n is selected from the group consisting of 0 and real numbers 1 to 5, with the provision that when n equals zero, A is not hydrogen.

12. A composition of matter according to claim 11 wherein $R_1$ and $R_2$ are ortho with respect to the phenolic hydroxyl group.

13. A composition of matter according to claim 11 wherein $R_1$ and $R_2$ are hydrogen and the phenolic hydroxyl group is para to the radical X.

14. A composition of matter according to claim 11 wherein $R_1$ and $R_2$ are tertiary-butyl radicals and ortho to the phenolic hydroxyl group.

15. A composition of matter according to claim 11 wherein X is a divalent dicyclopentadiene radical.

16. A composition of matter according to claim 11 wherein X is a divalent 2,5-norbornadiene radical.

17. A composition of matter according to claim 11 wherein X is a divalent methylene radical.

18. A composition of matter according to claim 11 that is 2-(2-hydroxy-3-tertiary-butyl-5-methylbenzyl)-4-methyl-6-tertiary-butyl phenyl-3-(4-hydroxy phenylthio)propionate.

19. A composition of matter according to claim 11 that is 3,5-ditertiary butyl-4-hydroxyphenyl-3-(4-hydroxyphenylthio)propionate.

20. A composition of matter according to claim 11 that is [3-(3,5-ditertiary butyl-4-hydroxyphenyl)-propyl]-3-(4-hydroxyphenylthio) propionate.

* * * * *